US011253595B2

(12) United States Patent
Siamon

(10) Patent No.: US 11,253,595 B2
(45) Date of Patent: *Feb. 22, 2022

(54) TREATMENT FOR REDUCING ADVERSE EVENTS INCLUDING CHEMOTHERAPY DISCOMFORT AND OTHER CONDITIONS

(71) Applicant: Al Siamon, Nipomo, CA (US)

(72) Inventor: Al Siamon, Nipomo, CA (US)

(73) Assignee: Al Siamon, Nipomo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/219,701

(22) Filed: Mar. 31, 2021

(65) Prior Publication Data

US 2021/0213131 A1 Jul. 15, 2021

Related U.S. Application Data

(63) Continuation-in-part of application No. 16/892,166, filed on Jun. 3, 2020, now Pat. No. 11,000,540.

(60) Provisional application No. 62/939,125, filed on Nov. 22, 2019.

(51) Int. Cl.

| | | |
|---|---|---|
| *A61K 47/02* | (2006.01) | |
| *A61P 39/00* | (2006.01) | |
| *A61K 9/00* | (2006.01) | |
| *A61K 31/282* | (2006.01) | |
| *A61K 33/243* | (2019.01) | |
| *A61K 31/675* | (2006.01) | |
| *A61K 31/337* | (2006.01) | |
| *A61K 31/704* | (2006.01) | |
| *A61K 31/7048* | (2006.01) | |
| *A61K 31/513* | (2006.01) | |
| *A61K 31/7068* | (2006.01) | |
| *A61K 31/519* | (2006.01) | |
| *A61K 31/395* | (2006.01) | |
| *A61K 38/14* | (2006.01) | |
| *A61K 31/475* | (2006.01) | |
| *A61K 31/655* | (2006.01) | |
| *A61K 9/08* | (2006.01) | |

(52) U.S. Cl.
CPC ............ *A61K 47/02* (2013.01); *A61K 9/0053* (2013.01); *A61K 9/08* (2013.01); *A61K 31/282* (2013.01); *A61K 31/337* (2013.01); *A61K 31/475* (2013.01); *A61K 31/513* (2013.01); *A61K 31/519* (2013.01); *A61K 31/5545* (2017.08); *A61K 31/655* (2013.01); *A61K 31/675* (2013.01); *A61K 31/704* (2013.01); *A61K 31/7048* (2013.01); *A61K 31/7068* (2013.01); *A61K 33/243* (2019.01); *A61K 38/14* (2013.01); *A61P 39/00* (2018.01)

(58) Field of Classification Search
CPC .... A61K 47/02; A61K 33/243; A61K 9/0053; A61K 9/08; A61K 38/14; A61K 31/282; A61K 31/5545; A61K 31/337; A61K 31/475; A61K 31/513; A61K 31/519; A61K 31/655; A61K 31/675; A61K 31/704; A61K 31/7048; A61K 31/7068; A61P 39/00

See application file for complete search history.

(56) References Cited

U.S. PATENT DOCUMENTS

| | | |
|---|---|---|
| 3,884,711 A | 5/1975 | Varsanyi et al. |
| 3,996,149 A | 12/1976 | Burke, Jr. |
| 4,064,067 A | 12/1977 | Lore |
| 4,082,558 A | 4/1978 | Nobuo |
| 4,115,307 A | 9/1978 | McGilvery |
| 4,212,761 A | 7/1980 | Ciaccio |
| 4,307,089 A | 12/1981 | Melloh |
| 4,504,995 A | 3/1985 | Zippwald, Sr. |
| 4,540,504 A | 9/1985 | Eoga |
| 4,592,892 A | 6/1986 | Ueno et al. |
| 4,642,192 A | 2/1987 | Heskett |
| 4,740,366 A | 4/1988 | Winston et al. |
| 4,828,621 A | 5/1989 | Siamon |
| 4,851,212 A | 7/1989 | Winston et al. |
| 4,995,418 A | 2/1991 | Cervola |
| 5,428,856 A | 7/1995 | Thorne |
| 5,434,182 A | 7/1995 | Isaacs et al. |
| 5,552,078 A | 9/1996 | Carr et al. |
| 5,635,462 A | 6/1997 | Fendler et al. |
| 5,770,089 A | 6/1998 | Kubo |
| 5,833,850 A | 11/1998 | Liu |
| 5,861,430 A | 1/1999 | Markonius |
| 5,928,671 A | 7/1999 | Domenico |
| 6,022,547 A | 2/2000 | Herb et al. |
| 6,046,160 A | 4/2000 | Obi-Tabot |
| 6,048,456 A | 4/2000 | Palmer |
| 6,184,198 B1 | 2/2001 | Siamon |
| 6,185,777 B1 | 2/2001 | Siamon |

(Continued)

OTHER PUBLICATIONS

Amy Quynh Trang Pham et al. "Drug Induced Metabolic Acidosis" in FI000Res, 2015) (Year: 2015).*
Wiklund et al., "Clinical Buffering of Metabolic Acidosis: Problems and a Solution" in Resuscitation, 12 (1985) 279-293. (Year: 1985).*
Max Harry Weil et al. "Management of Acidosis: The Role of Buffer Agents" in Critical Care 1997, 1(2). (Year: 1997).*
Ken Kondo et al. "Severe Acute Metabolic Acidosis and Wernicke's Encephalopathy Following Chemotherapy with 5-Fluorouracil and Cisplatin: Case Report and Review of the Literature," Jpn J Clin Oncol 26: 234-236, 1996. (Year: 1996).*

(Continued)

*Primary Examiner* — Blessing M Fubara
(74) *Attorney, Agent, or Firm* — Maschoff Brennan; Brent Johnson; David Old

(57) ABSTRACT

This disclosure relates to treatments for reducing the side effects associated with treatment of a medication or drug, such as a chemotherapy medication, being experienced by a patient. This may be accomplished by administering to a patient taking the medication, a buffered aqueous liquid having a pH of about 10 to about 11.5, wherein the buffered aqueous liquid comprises sodium bicarbonate, sodium carbonate, and trisodium phosphate.

21 Claims, No Drawings

(56) References Cited

U.S. PATENT DOCUMENTS

| | | |
|---|---|---|
| 6,217,887 B1 | 4/2001 | Beerse et al. |
| 6,225,279 B1 | 5/2001 | Siamon |
| 6,231,763 B1 | 5/2001 | Chau |
| 6,432,425 B1 | 8/2002 | Siamon |
| 6,506,392 B2 | 1/2003 | Siamon |
| 8,864,998 B1 | 10/2014 | Siamon |
| 2010/0234430 A1* | 9/2010 | Taneja ................. A61K 9/1623 514/338 |

OTHER PUBLICATIONS

Magro, M. et al., Alkaline Water and Longevity: a Murine Study, Evidence-Based Complementary and Alternative Medicine, vol. 2016, Article ID 3084126, 6 pages, bearing an alleged date of 2016, http://dx.doi.org/10.1155/2016/3084126.

Lea, P. et al., Ultrastructure Changes Induced by Dry Film Formation of a Trisodium Phosphate Blend, Antimicrobial Solution, Scanning: The Journal of Scanning Microscopies, 25(6), 277-284, bearing an alleged date of Nov. 2003.

Cleanshield customer testimonials, http://www.cleanshield.net/services.html and http://www.cleanshield.net/testimonials.html.

* cited by examiner

TREATMENT FOR REDUCING ADVERSE EVENTS INCLUDING CHEMOTHERAPY DISCOMFORT AND OTHER CONDITIONS

CROSS-REFERENCE TO RELATED APPLICATIONS

This application is a continuation-in-part of U.S. Non-Provisional application Ser. No. 16/892,166, filed Jun. 3, 2020, which claims the benefit of U.S. Provisional Application No. 62/939,125, filed Nov. 22, 2019, which are incorporated by reference herein in their entirety.

FIELD OF THE DISCLOSURE

This disclosure provides an orally administered treatment which ameliorates the side effects of chemotherapy on humans. More specifically, the disclosed treatment may completely negate a side effect of chemotherapy.

BACKGROUND OF THE DISCLOSURE

Chemotherapy is a well-known and potent treatment for many types of cancer. Chemotherapy can prolong a person's life and perhaps even rid them of cancer. However, there is a downside to chemotherapy. Some of the chemistry found in chemotherapy drugs cannot distinguish between normal cells and cancer cells, killing both, and causing the negative side effects. Most people will experience side effects, which are common with the administration of the potent compounds used in chemotherapy. The reactions are often unpredictable. Some of the more common reactions are general ill feeling, easy bruising or bleeding, hair loss, nausea and vomiting, difficulty in breathing, neuropathy, constipation and diarrhea.

Treating these side effects requires the administration of even more drugs in addition to the chemotherapy drugs. They may include antihistamines, corticosteroids, beclomethasone, bronchodilators and many other classes of drugs. All of these drugs may have their own negative side effects. The net result is that the patient is subjected to many different types of reactions that complicate the effectiveness of the chemotherapy medications.

The accompanying description will aid in the understanding of the described features and functionality of the disclosed treatment.

SUMMARY OF THE DISCLOSURE

The current disclosure relates to with various chemical compositions to address the problem of unwanted side effects resulting from drugs or medications such as chemotherapy. The disclosed compositions, and the combination of ingredients described herein, effectively achieve this goal. Namely, administering to a patient taking a medication, a buffered aqueous liquid having a pH of about 10 to about 11.5. This may dramatically reduce a side effect of a treatment, such as chemotherapy.

DETAILED DESCRIPTION

The medical community recognizes that low (or acidic) pH can contribute to health problems, and that raising a person's pH to be more alkaline, e.g. slightly above 7, such as 7.1-7.4 or 7.3, can improve an individual's health. The problem has been that highly alkaline solutions can be toxic to human beings, and that solutions that are only slightly alkaline do not have the capacity to have a significant effect upon pH.

The treatment is based on the principle that a buffered aqueous liquid having a pH of between 10 and 11.5 (such as about 10-10.3, about 10.3-10.6, about 10.6-10.9, about 10.9-11.2, about 11.2-11.5, about 10-10.5, about 10.5-11, or about 11-11.5) can be ingested, sprayed on the skin, or even sprayed in the eyes, causing no caustic reaction. A buffered aqueous liquid in this pH range can improve health by raising a person's pH without having the toxic effects associated with higher pHs. The pH of the disclosed products are within these acceptable ranges. For the purposes of this disclosure, a buffered aqueous liquid having a pH in one of the ranges above is referred to as a "subject composition."

Administering a subject composition to an animal, such as a human being, who has an adverse effect associated with taking a medication, has a profound effect of keeping the body in its best possible health condition. When the human body is in a pH state of 7.4 it is more resistant to harm. Most people are in a constant state of acidosis, which is the cause of the problems discussed herein. When the acidosis is eliminated, the body is in a better position to stay healthy. Additionally, when medication is taken in conjunction with the disclosed treatment, the negative side effects of the medications are dramatically reduced, including the negative side effects of chemotherapy.

In order to maintain this desired pH range, a person may orally consume the subject composition, which has a pH of approximately 11, to neutralize the acid in the body. The body then begins to produce additional acid, but at the same time it produces an equal amount of alkalinity. The net effect is that the body returns to a pH level of 7.4.

The subject composition may be used to reduce an adverse event associated with use of a medication. For the purposes of this disclosure, to "reduce" an adverse event or any negative side effect of a medication, includes reducing the adverse event or negative side effect that is already being experienced by the patient. Alternatively, if the subject composition is introduced before the adverse event or negative side effect to be reduced has occurred, to prevent the adverse event or negative side effect from occurring, or to reduce the severity of the adverse event or negative side effect as compared to what would have been experienced had the subject composition not been administered to the patient.

A subject composition may be prepared by adding an appropriate buffer or buffer combination to water or an aqueous solution. Suitable examples are listed in the table below. For some subject compositions, any buffer pair, or individual species from the buffer pair (e.g. carbonate), from the table below may be used. Additionally, combinations of buffer pairs (e.g. bicarbonate and carbonate plus phosphate dianion and phosphate trianion), combinations of individual species from buffer pairs (e.g. bicarbonate and phosphate trianion), or combinations of buffer pairs and individual species (e.g. bicarbonate and carbonate plus phosphate trianion) may be used.

| Buffer (Acid/Conjugate Base) | pKa of Acid (or pH of 1:1 mixture) |
| --- | --- |
| tris(hydroxymethyl)ammoniummethane/ Tris(hydroxymethyl)aminomethane (Tris) | 8.2 |
| tris(hydroxymethyl)methylamino]propanesulfonic acid/ tris(hydroxymethyl)methylamino]propanesulfonate TAPS | 8.55 |

-continued

| Buffer (Acid/Conjugate Base) | pKa of Acid (or pH of 1:1 mixture) |
|---|---|
| Boric Acid/Borate | 9.0 |
| N-Cyclohexyl-2-aminoethanesulfonic acid/N-Cyclohexyl-2-aminoethanesulfonate (CHES) | 9.3 |
| 3-(Cyclohexylamino)-2-hydroxypropane-1-sulfonic acid/3-(Cyclohexylamino)-2-hydroxypropane-1-sulfonate (CAPSO) | 9.6 |
| Glycine/Glycine anion | 9.60 |
| Isoleucine/Isoleucine anion | 9.60 |
| Leucine/Leucine anion | 9.60 |
| Valine/Valine anion | 9.62 |
| Alanine/Alanine anion | 9.69 |
| Bicarbonate/Carbonate | 10.32 |
| N-cyclohexyl-3-aminopropanesulfonic acid/N-cyclohexyl-3-aminopropanesulfonate (CAPS) | 10.4 |
| Lysine anion/Lysine dianion | 10.79 |
| Cysteine/Cysteine anion | 10.78 |
| Tyrosine anion/Tyrosine dianion | 10.07 |
| Proline/Proline anion | 10.60 |
| Phosphate dianion/Phosphate trianion | 12.3 |
| Arginine anion/Arginine dianion | 12.48 |

A pH of a buffer solution can be targeted using the Henderson-Hasselbach equation:

$$pH = pK_a + \log_{10}([Base]/[Acid])$$

The Henderson-Hasselbach is an estimate which may not be accurate in all situations, but is sufficiently close to reach the desired pH with routine experimentation. Thus, since the $\log_{10}$ of 1 is 0, the pH is roughly the $pK_a$ when the acid and its conjugate base are added in equal amounts.

The pH of any buffer system may be tuned by adding a strong acid, such as HCl, HBr, HI, $H_2SO_4$, $H_3PO_4$, etc. to reduce the pH, or a strong base, such as NaOH, KOH, etc., to increase the pH. Thus, ions such as $Cl^-$, $Br^-$, $I^-$, $SO_4^{2-}$, $H_2PO_4^-$, $Na^+$, $K^+$, etc., may be present in the subject composition. Ions may also be added for other purposes, such as adjusting tonicity, providing electrolyte balance, etc.

For the conjugate bases or salt forms of the buffer compounds in the table above, or for any buffer systems, suitable cationic counter-ions may include sodium, potassium, calcium, magnesium, lithium, etc. In some embodiments, at least one of the cationic counterions is $Na^+$. In some embodiments, at least one of the cationic counterions is $K^+$. In some embodiments, at least one of the cationic counterions is $Ca^{2+}$. In some embodiments, at least one of the cationic counterions is $Mg^{2+}$.

Any buffer pair, including those recited herein, can be prepared by adding a single species, either in an acid or base form, to water or an aqueous solution, and adjusting the pH by adding an appropriate amount of a strong acid, e.g. HCl, or a strong base, e.g. NaOH. For example, a mixture of sodium bicarbonate and sodium carbonate can be prepared by adding NaOH to an aqueous solution of sodium bicarbonate.

In some embodiments, the aqueous solution comprises hydrogen bond activated water. Hydrogen bond activated water is water having its hydrogen bonding structure altered by adding a slight charge to the water. It is believed that the water molecules cluster around the charges, thus reducing the number of hydrogen bonds in the water's intermolecular structure. As a result, it has been observed that the activated water can have an alkaline pH using a smaller amount of buffer. Hydrogen bond activated water may be obtained, for example, by treating water with ceramic particles. One method of accomplishing this is by treating the water with a device described in U.S. Pat. No. 8,864,998, issued on Oct. 21, 2014 to Al Siamon, which is incorporated by reference in its entirety.

Any suitable amount of buffer may be used in the subject composition. In some embodiments, the total amount of buffer in the subject composition may be about 0.01-1 moles/L, about 0.01-0.1 moles/L, about 0.1-0.2 moles/L, about 0.2-0.3 moles/L, about 0.3-0.4 moles/L, about 0.4-0.5 moles/L, about 0.5-0.6 moles/L, about 0.6-0.7 moles/L, about 0.7-0.8 moles/L, about 0.8-0.9 moles/L, about 0.9-1 moles/L, about 0.01-0.3 moles/L, about 0.3-0.6 moles/L, about 0.6-1 moles/L, or about 0.1-0.3 moles/L.

The subject composition is administered orally to the patent, for example, in about 0.1-3 oz, about 0.1-2 oz, about 0.1-0.4 oz, about 0.4-0.8 oz, about 0.8-1.2 oz, about 1.2-1.6 oz, about 1.6-2 oz, or about 1-ounce portions. Each portion is administered 1 or more times per day, such as about 1, 2, 3, 4, 5, or 6 times per day spaced over the waking hours. In some embodiments, each portion is administered 3 times per day spaced over the waking hours. Treatment may be continued for as long as the medication is taken, such as about 1 day to 1 week, about 1-2 weeks, about 2-4 weeks, about 1-3 months, about 3-6 months, about 6-9 months, about 9-12 months, about 1-2 years, about 2-5 years, about 5-10 years, or longer.

In some embodiments, a total of about 0.001-1 moles, about 0.001-0.1 moles, about 0.001-0.02 moles, about 0.02-0.04 moles, about 0.04-0.06 moles, about 0.06-0.08 moles, about 0.08-0.1 moles, about 0.1-0.3 moles, about 0.3-0.6 moles, or about 0.6-1 moles of buffer may be administered over the course of a chemotherapy treatment, or over a period of about 1-2 or 2-3 months for a medication that is administered over a long period of time for a chronic condition.

While a medication or drug may potentially be administered in a subject composition, it may be helpful to administer a subject composition separately from the medication or drug, or to have the drug or medication not be present in the subject composition. Similarly, while a drug or medication may be administered at the same time as a subject composition, it may be helpful to administer a subject composition at a different time than, or some time before and/or after, the medication or drug. In some embodiments, the drug or medication is administered before and/or after the subject composition, such as at least about 30 minutes, at least about 1 hour, at least about 1.5 hours, at least about 2 hours, at least about 2.5 hours, at least about 3 hours, or at least about 4 hours, before and/or after the medication or drug is administered. This may be important for many orally administered medications or drugs because the bioavailability of medications or drugs can be affected by stomach pH, and administering the subject composition may significantly increase stomach pH. Additionally, some medications or drugs may reduce the pH of the subject composition in a way that reduces its effectiveness.

In some embodiments, the subject composition contains a bicarbonate (such as sodium bicarbonate) and at least one other buffering compound, such as an acid or conjugate base in the table above. In some embodiments, the subject composition contains a carbonate (such as sodium carbonate) and at least one other buffering compound, such as an acid or conjugate base in the table above. In some embodiments, the subject composition contains a bicarbonate (such as sodium bicarbonate) and a carbonate (such as sodium carbonate) and at least one other buffering compound, such as an acid or conjugate base in the table above. In some embodiments, the subject composition contains $PO_4^{3-}$ or a phosphate, e.g. trisodium phosphate, and at least one other buffering compound, such as an acid or conjugate base in the table above.

In some embodiments, a combination of a bicarbonate, such as sodium bicarbonate, a carbonate, such as sodium carbonate, and a phosphate, such as trisodium phosphate are used to achieve the desired target pH. In embodiments comprising a combination of a bicarbonate, such as sodium bicarbonate, a carbonate, such as sodium carbonate, and a phosphate, such as trisodium phosphate, the three separate ingredients are mixed into a liquid comprising primarily potable water. It may be important to avoid adding acidic additives such as flavorings or fruit juices, because they may lower the pH value to the point of making the treatment ineffective. The ingredients may be added in any order and the quantities of each may be only approximately equal. The treatment will perform adequately whether the amounts of each ingredient are exactly the same or if there is a variation of up to 50%, or possibly more. The total of the three ingredients should be approximately 0.05-2 gm/oz, 0.05-0.2 gm/oz, about 0.2-0.4 gm/oz, about 0.4-0.6 gm/oz, about 0.6-0.8 gm/oz, about 0.8-1 gm/oz, about 1-1.4 gm/oz, about 1.4-2 gm/oz, about 0.3-0.7 gm/oz, or about 0.5 gm/oz of fluid. The resulting mixture is then administered orally to the patent, e.g., in about 0.1-3 oz, about 0.1-2 oz, about 0.1-0.4 oz, about 0.4-0.8 oz, about 0.8-1.2 oz, about 1.2-1.6 oz, about 1.6-2 oz, or about 1-ounce portions. Each portion is administered 1 or more times a day, such as about 1, 2, 3, 4, or 5 times per day spaced over the waking hours. In some embodiments, each portion is administered 3 times per day spaced over the waking hours (e.g. at 4-6 hour intervals).

In some embodiments, a total of about 0.001-1 moles, about 0.001-0.1, about 0.001-0.02 moles, about 0.02-0.04 moles, about 0.04-0.06 moles, about 0.06-0.08 moles, about 0.08-0.1 moles, about 0.1-0.3 moles, about 0.3-0.6 moles, or about 0.6-1 moles of buffer (i.e. moles of bicarbonate+moles of carbonate+moles of phosphate) may be administered over the course of a chemotherapy treatment, or over a period of about 1-2 or 2-3 months for a medication that is administered over a long period of time for a chronic condition.

In some embodiments, a subject composition comprises the following ingredients.
1. bicarbonate of soda ($NaHCO_3$ or sodium bicarbonate), in an amount that is about 16-67%, about 16-25%, about 25-35%, about 35-45%, about 45-55%, about 55-67%, or about ⅓ of the total weight of $NaHCO_3$, $Na_2CO_3$, and $Na_3PO_4$;
2. soda ash ($Na_2CO_3$ or sodium carbonate), in an amount that is about 16-67%, about 16-25%, about 25-35%, about 35-45%, about 45-55%, about 55-67%, or about ⅓ of the total weight of $NaHCO_3$, $Na_2CO_3$, and $Na_3PO_4$; and
3. trisodium phosphate ($Na_3PO_4$), in an amount that is about 16-67%, about 16-25%, about 25-35%, about 35-45%, about 45-55%, about 55-67%, or about ⅓ of the total weight of $NaHCO_3$, $Na_2CO_3$, and $Na_3PO_4$.

These three ingredients are added in close time proximity to each other and mixed uniformly into the liquid at ambient temperature. The quantities of the three ingredients are adjusted depending on the quantity of liquid to which the ingredients will be added. For example, for each gallon of liquid, a total amount of additive that is 64 grams (or about 0.07 moles/L of sodium bicarbonate, about 0.05 moles/L of sodium carbonate, and about 0.03 moles/L of trisodium phosphate, for a total of about 0.15 moles/L of buffer) may be desirable. As mentioned above, the quantities of each of these three compounds may be varied up or down by 50% (fifty percent), or possibly more, without destroying the benefits of the treatment.

Quite surprisingly, this simple treatment may significantly alter body chemistry, reducing or eliminating the discomfort and side effects of chemotherapy.

A subject composition may be used to reduce adverse events or side effects associated with use of an active pharmaceutical ingredient, drug, or medication. For example, a subject composition may be administered in conjunction with one or more of the following drugs to reduce adverse events: abacavir sulfate, abaloparatide, abemaciclib, abiraterone acetate, acalabrutinib, acamprosate calcium, acarbose, acebutolol hydrochloride, acetaminophen, acetazolamide, acetazolamide sodium, acetohydroxamic acid, acetylcholine chloride, acetylcysteine, acitretin, aclidinium bromide, acrivastine, acyclovir sodium, adapalene, adefovir dipivoxil, adenosine, afatinib dimaleate, albendazole, albumin human, albumin iodinated I-125 serum, albumin iodinated I-131 serum, albuterol sulfate, alcaftadine, alclometasone dipropionate, alectinib hydrochloride, alendronate sodium, alfentanil hydrochloride, alfuzosin hydrochloride, aliskiren hemifumarate, alitretinoin, allopurinol, allopurinol sodium, almotriptan malate, alogliptin benzoate, alosetron hydrochloride, alpha-tocopherol acetate, alprazolam, alprostadil, altretamine, aluminum hydroxide, alvimopan, amantadine hydrochloride, ambrisentan, amcinonide, amifostine, amikacin sulfate, amiloride hydrochloride, aminocaproic acid, aminolevulinic acid hydrochloride, aminophylline, aminosalicylic acid, amiodarone hydrochloride, amitriptyline hydrochloride, amlodipine hydrochlorothiazide, amlodipine besylate, ammonium lactate, amoxapine, amoxicillin, clarithromycin, AMP aspartate, amphetamine, amphetamine aspartate, amphetamine sulfate, amphotericin B, ampicillin sodium, ampicillin/ampicillin trihydrate, anagrelide hydrochloride, anastrozole, angiotensin II acetate, anidulafungin, apalutamide, apixaban, apomorphine hydrochloride, apraclonidine hydrochloride, apremilast, aprepitant, arformoterol tartrate, argatroban, arginine hydrochloride, aripiprazole, aripiprazole lauroxil, armodafinil, arsenic trioxide, artemether, articaine hydrochloride, asenapine maleate, aspirin, codeine phosphate, atazanavir sulfate, atenolol, atomoxetine hydrochloride, atorvastatin calcium, atovaquone, atracurium besylate, atropine, atropine sulfate, auranofin, avanafil, avatrombopag maleate, avibactam sodium, avobenzone, axitinib, azacytidine, azathioprine, azathioprine sodium, azelaic acid, azelastine hydrochloride, azilsartan kamedoxomil, azithromycin, aztreonam, bacitracin, bacitracin zinc, baclofen, balsalazide disodium, baricitinib, barium sulfate, bazedoxifene acetate, beclomethasone dipropionate, beclomethasone dipropionate monohydrate, bedaquiline fumarate, belinostat, benazepril hydrochloride, bendamustine hydrochloride, bendroflumethiazide, benoxinate hydrochloride, bentoquatam, benznidazole, benzonatate, benzoyl peroxide, benzphetamine hydrochloride, benztropine mesylate, benzyl alcohol, benzylpenicilloyl polylysine, bepotastine besilate, beractant, besifloxacin hydrochloride, betaine, betamethasone acetate, betamethasone dipropionate, betamethasone sodium phosphate, betamethasone valerate, bethanechol chloride, betrixaban, bexarotene, bicalutamide, bictegravir sodium, bimatoprost, binimetinib, bismuth subcitrate potassium, bisoprolol fumarate, bivalirudin, bleomycin sulfate, bortezomib, bosentan, bosutinib monohydrate, brexpiprazole, brigatinib, brimonidine tartrate, brinzolamide, brivaracetam, bromfenac sodium, bromocriptine mesylate, brompheniramine maleate, budesonide, bumetanide, bupivacaine, bupivacaine hydrochloride, buprenorphine, buprenorphine hydrochloride, bupropion hydrobromide, bupropion hydrochloride, buspirone hydrochloride, busulfan, butabarbital sodium, butenafine hydrochloride, butenafine hydrochloride, butoconazole nitrate, butorphanol tartrate, cabazitaxel, cabergoline, cabozantinib S-malate, caffeine, dihydrocodeine bitartrate, caffeine citrate, calcifediol, calcipotriene, calcitonin salmon, calcitriol, calcium acetate, calcium carbonate, calcium chloride, calcium gluconate, calfactant, canagliflozin, candesartan cilexetil, cangrelor, capecitabine, capreomycin sulfate, capsaicin, captopril, carbachol, carbamazepine, carbidopa, carbinoxamine maleate, carboplatin, carboprost tromethamine, carfilzomib, carglumic acid, cariprazine hydrochloride, carisoprodol, carmustine, carteolol hydrochloride, carvedilol, carvedilol phosphate, caspofungin acetate, cefaclor, cefadroxil, cefadroxil hemihydrate, cefazolin sodium, cefdinir, cefepime hydrochloride, cefixime, cefotaxime sodium, cefotetan disodium, cefoxitin sodium, cefpodoxime proxetil, cefprozil, ceftaroline fosamil, ceftazidime, ceftolozane sulfate, ceftriaxone sodium, cefuroxime axetil, cefuroxime sodium, celecoxib, cephalexin, ceritinib, cetirizine hydrochloride, cetrorelix, cevimeline hydrochloride, chenodiol, chlorambucil, chloramphenicol sodium succinate, chlordiazepoxide hydrochloride, chlorhexidine gluconate, chloroprocaine hydrochloride, chloroquine phosphate, chlorothiazide, chlorothiazide sodium, chlorpheniramine maleate, chlorpheniramine maleate, pseudoephedrine hydrochloride, chlorpheniramine polistirex, chlorpromazine hydrochloride, chlorpropamide, chlorthalidone, chlorzoxazone, cholestyramine, cholic acid, choline c-11, choline fenofibrate, choriogonadotropin alfa, chorionic, chromic chloride, ciclesonide, ciclopirox, cidofovir, cilastatin sodium, cilostazol, cimetidine, cimetidine hydrochloride, cinacalcet hydrochloride, ciprofloxacin, ciprofloxacin hydrochloride, cisatracurium besylate, cisplatin, citalopram hydrobromide, citric acid, cladribine, clarithromycin, clemastine fumarate, clevidipine, clindamycin hydrochloride, clindamycin palmitate hydrochloride, clindamycin phosphate, clobazam, clobetasol propionate, clocortolone pivalate, clofarabine, clomiphene citrate, clomipramine hydrochloride, clonazepam, clonidine, clonidine hydrochloride, clopidogrel bisulfate, clorazepate dipotassium, clotrimazole, clozapine, cobicistat, cobimetinib fumarate, cocaine hydrochloride, codeine phosphate, codeine sulfate, colchicine, colesevelam hydrochloride, colestipol hydrochloride, colistimethate sodium, colistin sulfate, conivaptan hydrochloride, copanlisib dihydrochloride, corticorelin ovine triflutate, corticotropin, cortisone acetate, cosyntropin, crisaborole, crizotinib, crofelemer, cromolyn sodium, crotamiton, cupric chloride, cyanocobalamin, cyclobenzaprine hydrochloride, cyclopentolate hydrochloride, cyclophosphamide, cycloserine, cyclosporine, cyproheptadine hydrochloride, cysteamine bitartrate, cysteamine hydrochloride, cytarabine, dabigatran etexilate mesylate, dabrafenib mesylate, dacarbazine, daclatasvir dihydrochloride, dactinomycin, dalbavancin hydrochloride, dalfampridine, dalfopristin, dalteparin sodium, danazol, dantrolene sodium, dapagliflozin, dapsone, daptomycin, darifenacin hydrobromide, darunavir ethanolate, dasabuvir sodium, dasatinib, daunorubicin hydrochloride, decitabine, deferasirox, deferiprone, deferoxamine mesylate, defibrotide sodium, deflazacort, degarelix acetate, delafloxacin meglumine, delavirdine mesylate, demeclocycline hydrochloride, deoxycholic acid, desflurane, desipramine hydrochloride, desirudin recombinant, desloratadine, desmopressin acetate, desogestrel, desonide, desoximetasone, desvenlafaxine, desvenlafaxine succinate, deutetrabenazine, dexamethasone, dexamethasone sodium phosphate, dexchlorpheniramine maleate, dexlansoprazole, dexmedetomidine hydrochloride, dexmethylphenidate hydrochloride, dexrazoxane hydrochloride, dextroamphetamine sulfate, dextromethorphan, dextromethorphan hydrobromide, dextromethorphan polistirex, dextrose, diatrizoate meglumine, diazepam, diazoxide, dichlorphenamide, diclofenac, diclofenac epolamine, diclofenac potassium, diclofenac sodium, dicloxacillin sodium, dicyclomine hydrochloride, didanosine, dienogest, diethylpropion hydrochloride, diflorasone diacetate, diflunisal, difluprednate, digoxin, dihydroergotamine mesylate, diltiazem hydrochloride, dimenhydrinate, dimercaprol, dimethyl fumarate, dimethyl sulfoxide, dinoprostone, diphenhydramine citrate, diphenhydramine hydrochloride, dipyridamole, disopyramide phosphate, disulfiram, divalproex sodium, dobutamine hydrochloride, docetaxel, docosanol, dofetilide, dolutegravir sodium, donepezil hydrochloride, dorzolamide hydrochloride, doxapram hydrochloride, doxazosin mesylate, doxepin hydrochloride, doxercalciferol, doxorubicin hydrochloride, doxycycline, doxycycline calcium, doxycycline hyclate, doxylamine succinate, dronabinol, dronedarone hydrochloride, droperidol, drospirenone, droxidopa, duloxetine hydrochloride, dutasteride, echothiophate iodide, econazole nitrate, edaravone, edetate calcium disodium, edoxaban tosylate, edrophonium chloride, efavirenz, efinaconazole, eflornithine hydrochloride, elbasvir, eletriptan hydrobromide, eliglustat tartrate, eltrombopag olamine, eluxadoline, emedastine difumarate, empagliflozin, emtricitabine, enalapril maleate, enalaprilat, enasidenib mesylate, encorafenib, enfuvirtide, enoxaparin sodium, entacapone, entecavir, enzalutamide, ephedrine sulfate, epinastine hydrochloride, epinephrine, epinephrine bitartrate, epirubicin hydrochloride, eplerenone, epoprostenol sodium, eprosartan mesylate, eptifibatide, ergocalciferol, ergoloid mesylates, ergotamine tartrate, eribulin mesylate, erlotinib hydrochloride, ertapenem sodium, ertugliflozin, erythromycin, erythromycin ethylsuccinate, erythromycin lactobionate, erythromycin stearate, escitalopram oxalate, eslicarbazepine acetate, esmolol hydrochloride, esomeprazole magnesium, esomeprazole sodium, esomeprazole strontium, estazolam esterified, estradiol, estradiol acetate, estradiol cypionate, estradiol valerate, estramustine phosphate sodium, estrogens, estropipate, eszopiclone, etelcalcetide, eteplirsen, ethacrynate sodium, ethacrynic acid, ethambutol hydrochloride, ethanolamine oleate, ethinyl estradiol, levomefolate calcium, ethiodized oil, ethionamide, ethosuximide, ethotoin, etidronate disodium, etodolac, etomidate, etonogestrel, etoposide, etoposide phosphate, etravirine, everolimus, exemestane, exenatide, exenatide synthetic, ezetimibe, famciclovir, famotidine, febuxostat, felbamate, felodipine, fenofibrate, fenofibric acid, fenoldopam mesylate, fenoprofen calcium, fentanyl, fentanyl citrate, ferric carboxymaltose, ferric citrate, ferric hexacyanoferrate(II), ferric pyrophosphate citrate, ferumoxytol, fesoterodine fumarate, fexofenadine hydrochloride, fidaxomicin, finafloxacin, finasteride, fingolimod hydrochloride, fish oil, flavoxate hydrochloride, flecainide acetate, flibanserin, florbetaben F-18, florbetapir F-18, floxuridine, fluciclovine F-18, fluconazole, flucytosine, fludarabine phosphate, fludeoxyglucose F-18, fludrocortisone acetate, flumazenil, flunisolide, fluocinolone acetonide, fluocinonide, fluorescein sodium, fluorometholone, fluorometholone acetate, fluorouracil, fluoxetine hydrochloride, fluoxymesterone, fluphenazine decanoate, fluphenazine hydrochloride, flurandrenolide, flurazepam hydrochloride, flurbiprofen, flurbiprofen sodium, flutamide, flutemetamol F-18, fluticasone furoate, fluticasone propionate, fluvastatin sodium, fluvoxamine maleate, folic acid, follitropin alfa/beta, fomepizole, fondaparinux sodium, formoterol fumarate, fosamprenavir calcium, fosaprepitant dimeglumine, foscarnet sodium, fosfomycin tromethamine, fosinopril sodium, fosnetupitant chloride, fosphenytoin sodium, fostamatinib disodium, frovatriptan succinate, fulvestrant, furosemide, gabapentin, gabapentin enacarbil, gadobenate dimeglumine, gadobutrol, gadodiamide, gadopentetate dimeglumine, gadoterate meglumine, gadoteridol, gadoversetamide, gadoxetate disodium, galantamine hydrobromide, gallium citrate Ga-67, gallium dotatate Ga-68, ganciclovir, ganciclovir sodium, ganirelix acetate, gatifloxacin, gefitinib, gemcitabine hydrochloride, gemfibrozil, gemifloxacin mesylate, gentamicin sulfate, glatiramer acetate, glecaprevir, glimepiride, glipizide, glucagon, glucagon hydrochloride, glyburide, glycerol phenylbutyrate, glycopyrrolate, glycopyrronium tosylate, gonadotropin, goserelin acetate, gramicidin, granisetron, granisetron hydrochloride, griseofulvin, guaifenesin, guanabenz acetate, guanfacine hydrochloride, guanidine hydrochloride, halcinonide, halobetasol propionate, haloperidol, haloperidol decanoate, haloperidol lactate, heparin sodium, hexachlorophene, hexaminolevulinate hydrochloride, histrelin acetate, homatropine methylbromide, hyaluronidase, hyaluronidase recombinant human, hydralazine hydrochloride, hydrochlorothiazide, hydrocodone bitartrate, hydrocortisone, hydrocortisone acetate, hydrocortisone butyrate, hydrocortisone probutate, hydrocortisone sodium succinate, hydrocortisone valerate, hydromorphone hydrochloride, hydroxocobalamin, hydroxyamphetamine hydrobromide, hydroxychloroquine sulfate, hydroxyprogesterone caproate, hydroxypropyl cellulose, hydroxyurea, hydroxyzine hydrochloride, hydroxyzine pamoate, ibandronate sodium, ibrutinib, ibuprofen, ibuprofen lysine, ibuprofen sodium, ibutilide fumarate, icatibant acetate, icodextrin, icosapent ethyl, idarubicin hydrochloride, idelalisib, ifosfami de, iloperidone, iloprost, imatinib mesylate, imiglucerase, imipramine hydrochloride, imipramine pamoate, imiquimod, inamrinone lactate, indacaterol maleate, indapamide, indinavir sulfate, indium In-111 chloride, indium In-111 oxyquinoline, indium In-111 pentetate disodium, indium In-111 pentetreotide kit, indocyanine green, indomethacin, indomethacin sodium, ingenol mebutate, insulin aspart, insulin aspart protamine recombinant, insulin aspart recombinant, insulin degludec, insulin detemir recombinant, insulin glargine, insulin glargine recombinant, insulin glulisine recombinant, insulin human, insulin lispro, insulin lispro recombinant, insulin recombinant human, insulin susp isophane recombinant human, iobenguane sulfate 1-123, iodine povacrylex, iodixanol, ioflupane 1-123, iohexol, iopamidol, iopromide, iothalamate meglumine, iothalamate sodium i-125, ioversol, ipratropium bromide, irbesartan, irinotecan hydrochloride, iron dextran, iron sucrose, isavuconazonium sulfate, isocarboxazid, isoflurane, isoniazid, isoproterenol hydrochloride, isosorbide dinitrate, isosorbide mononitrate, isosulfan blue, isotretinoin, isradipine, itraconazole, ivabradine hydrochloride, ivacaftor, ivermectin, ixabepilone, ixazomib citrate, ketamine hydrochloride, ketoconazole, ketoprofen, ketorolac tromethamine, ketotifen fumarate, labetalol hydrochloride, lacosamide, lactulose, lamivudine, lamotrigine, lanreotide acetate, lansoprazole, lanthanum carbonate, lapatinib ditosylate, latanoprost, latanoprostene bunod, ledipasvir, leflunomide, lenalidomide, lenvatinib mesylate, lesinurad, letermovir, letrozole, leucovorin calcium, leuprolide acetate, levalbuterol hydrochloride, levalbuterol tartrate, levetiracetam, levobunolol hydrochloride, levocarnitine, levocetirizine dihydrochloride, levodopa entacapone, levofloxacin, levo-leucovorin calcium, levomilnacipran hydrochloride, levonordefrin, levonorgestrel, levorphanol tartrate, levothyroxine sodium, L-glutamine, lidocaine, lidocaine hydrochloride, lifitegrast, linaclotide, linagliptin, lincomycin hydrochloride, lindane, linezolid, liothyronine sodium, liotrix, liraglutide recombinant, lisdexamfetamine dimesylate, lisinopril, lithium carbonate, lithium citrate, lixisenatide, lodoxamide tromethamine, lofexidine hydrochloride, lomitapide mesylate, lomustine, loperamide hydrochloride, lopinavir, loratadine, lorazepam, lorcaserin hydrochloride, losartan potassium, loteprednol etabonate, lovastatin, loxapine, loxapine succinate, lubiprostone, luliconazole, lurasidone hydrochloride, lutetium dotatate Lu-177, macimorelin acetate, macitentan, mafenide acetate, magnesium chloride, magnesium sulfate, malathion, manganese chloride, maprotiline hydrochloride, maraviroc, mebendazole, mecamylamine hydrochloride, mecasermin recombinant, mechlorethamine hydrochloride, meclizine hydrochloride, meclofenamate sodium, medroxyprogesterone acetate, mefenamic acid, mefloquine hydrochloride, megestrol acetate, meloxicam, melphalan, melphalan hydrochloride, memantine hydrochloride, menotropins, menthol, meperidine hydrochloride, mepivacaine hydrochloride, meprobamate, mercaptopurine, meropenem, mesalamine, mesna, mestranol, metaproterenol sulfate, metaxalone, metformin hydrochloride, methacholine chloride, methadone hydrochloride, methamphetamine hydrochloride, methazolamide, methenamine hippurate, methimazole, methocarbamol, methohexital, sodium, methotrexate, methotrexate sodium, methoxsalen, methscopolamine bromide, methsuximide, methyclothiazide, methyldopa, methyldopate hydrochloride, methylene blue, methylergonovine, maleate, methylnaltrexone bromide, methylphenidate, methylphenidate hydrochloride, methylprednisolone, methylprednisolone acetate, methylprednisolone sodium succinate, methyltestosterone, metipranolol hydrochloride, metoclopramide hydrochloride, metolazone, metoprolol succinate, metoprolol tartrate, metronidazole, metyrapone, metyrosine, mexiletine hydrochloride, micafungin sodium, miconazole, miconazole nitrate, midazolam hydrochloride, midodrine hydrochloride, midostaurin, mifepristone, miglitol, miglustat, milnacipran hydrochloride, milrinone lactate, miltefosine, minocycline hydrochloride, minoxidil, mirabegron, mirtazapine, misoprostol, mitomycin, mitotane, mitoxantrone hydrochloride, modafinil, moexipril hydrochloride, molindone hydrochloride, mometasone furoate, montelukast sodium, morphine sulfate, moxidectin, moxifloxacin, moxifloxacin hydrochloride, mupirocin, mupirocin calcium, mycophenolate mofetil, mycophenolate mofetil hydrochloride, mycophenolic acid, nabilone, nabumetone, nadolol, nafarelin acetate, nafcillin sodium, naftifine hydrochloride, nalbuphine hydrochloride, naldemedine tosylate, naloxegol oxalate, naloxone hydrochloride, naltrexone, naltrexone hydrochloride, nandrolone decanoate, naphazoline hydrochloride, naproxen, naproxen sodium, naratriptan hydrochloride, natamycin, nateglinide, nebivolol hydrochloride, nedocromil sodium, nefazodone hydrochloride, nelarabine, nelfinavir mesylate, neomycin sulfate, neostigmine methylsulfate, nepafenac, neratinib maleate, nesiritide recombinant, netarsudil dimesylate, netupitant, nevirapine, niacin, nicardipine hydrochloride, nicotine, nicotine polacrilex, nifedipine, nilotinib hydrochloride, nilutamide, nimodipine, nintedanib esylate, niraparib tosylate, nisoldipine, nitazoxanide, nitisinone, nitrofurantoin, nitroglycerin, nizatidine, nonoxynol-9, norepinephrine bitartrate, norethindrone, norethindrone acetate, nortriptyline hydrochloride, nusinersen sodium, nystatin, obeticholic acid, octreotide acetate, ofloxacin, olanzapine, olanzapine pamoate, olaparib, olmesartan medoxomil, olodaterol hydrochloride, olopatadine hydrochloride, olsalazine sodium, omacetaxine mepesuccinate, ombitasvir, omega-3-acid ethyl esters, omeprazole, omeprazole magnesium, ondansetron, ondansetron hydrochloride, oritavancin diphosphate, orlistat, orphenadrine citrate, oseltamivir phosphate, osimertinib mesylate, ospemifene, oxacillin sodium, oxaliplatin, oxandrolone, oxaprozin, oxazepam, oxcarbazepine, oxiconazole nitrate, oxtriphylline, oxybutynin, oxybutynin chloride, oxycodone, oxycodone hydrochloride, oxymetazoline hydrochloride, oxymetholone, oxymorphone hydrochloride, oxytetracycline hydrochloride, oxytocin, ozenoxacin, paclitaxel, palbociclib, paliperidone, paliperidone palmitate, palonosetron hydrochloride, pamidronate disodium, pancrelipase, pancuronium bromide, panobinostat lactate, pantoprazole sodium, paricalcitol, paromomycin sulfate, paroxetine hydrochloride, paroxetine mesylate, pasireotide diaspartate, pasireotide pamoate, patiromer sorbitex calcium, pazopanib hydrochloride, pegademase bovine, pegaptanib sodium, pegvisomant, pemetrexed disodium, penciclovir, penicillamine, penicillin G benzathine, penicillin G potassium, penicillin G procaine, penicillin G sodium, penicillin V potassium, pentamidine isethionate, pentetate calcium trisodium, pentetate zinc trisodium, pentobarbital sodium, pentosan polysulfate sodium, pentostatin, pentoxifylline, peramivir, perampanel, perflutren, perindopril erbumine, permethrin, perphenazine, phendimetrazine tartrate, phenelzine sulfate, phenoxybenzamine hydrochloride, phentermine hydrochloride, phentolamine mesylate, phenylephrine hydrochloride, codeine phosphate, phenytoin, phenytoin sodium, phytonadione, pilocarpine hydrochloride, pimavanserin tartrate, pimecrolimus, pimozide, pindolol, pioglitazone hydrochloride, piperacillin sodium, pirfenidone, piroxicam, pitavastatin calcium, pitavastatin magnesium, plazomicin sulfate, plecanatide, plerixafor, podofilox, polidocanol, polyethylene glycol 3350, polymyxin B sulfate, pomalidomide, ponatinib hydrochloride, poractant alfa, porfimer sodium, posaconazole, potassium acetate, potassium chloride, potassium citrate, potassium iodide, povidone-iodine, pralatrexate, pralidoxime chloride, pramipexole dihydrochloride, pramlintide acetate, prasterone, prasugrel hydrochloride, pravastatin sodium, praziquantel, prazosin hydrochloride, prednicarbate, prednisolone, prednisolone acetate, prednisolone sodium phosphate prednisone, pregabalin, prilocaine hydrochloride, primaquine phosphate, primidone, probenecid, procainamide hydrochloride, procarbazine hydrochloride, prochlorperazine, prochlorperazine edisylate, prochlorperazine maleate, progesterone, promethazine hydrochloride, propafenone hydrochloride, propantheline bromide, proparacaine hydrochloride, propofol, propranolol hydrochloride, propylthiouracil, protamine sulfate, protriptyline hydrochloride, pseudoephedrine hydrochloride, dextromethorphan hydrobromide, pseudoephedrine sulfate, pyrazinamide, pyridostigmine bromide, pyridoxine hydrochloride, pyrimethamine, quazepam, quetiapine fumarate, quinapril hydrochloride, quinidine gluconate, quinidine sulfate, quinine sulfate, rabeprazole sodium, radium Ra-223 dichloride, raloxifene hydrochloridem, raltegravir potassium, ramelteon, ramipril, ranitidine hydrochloride, ranolazine, rasagiline mesylate, regadenoson, regorafenib, remifentanil hydrochloride, repaglinide, retapamulin, ribavirin, ribociclib succinate, riboflavin 5'-phosphate sodium, rifabutin, rifampin, rifapentine, rifaximin, rilpivirine hydrochloride, riluzole, rimantadine hydrochloride, riociguat, risedronate sodium, risperidone, ritonavir, rivaroxaban, rivastigmine, rivastigmine tartrate, rizatriptan benzoate, rocuronium bromide, rofecoxib, roflumilast, rolapitant hydrochloride, romidepsin, ropinirole hydrochloride, ropivacaine hydrochloride, rosiglitazone maleate, rosuvastatin calcium, rotigotine, rubidium chloride Rb-82, rucaparib camsylate, rufinamide, ruxolitinib phosphate, sacrosidase, sacubitril, safinamide mesylate, salmeterol xinafoate, samarium Sm-153 lexidronam pentasodium, sapropterin dihydrochloride, saquinavir mesylate, saxagliptin hydrochloride, scopolamine, secnidazole, secobarbital sodium, secretin synthetic human, selegiline, selegiline hydrochloride, selenium sulfide, selexipag, semaglutide, sertaconazole nitrate, sertraline hydrochloride, sevelamer carbonate, sevelamer hydrochloride, sevoflurane, sildenafil citrate, silodosin, silver sulfadiazine, simvastatin, sincalide, sinecatechins, sirolimus, sitagliptin phosphate, sodium acetate, sodium benzoate, sodium bicarbonate, sodium ferric gluconate complex, sodium fluoride, sodium fluoride F-18, sodium iodide 1-123, sodium iodide i-131, sodium lactate, sodium nitrite, sodium nitroprusside, sodium oxybate, sodium phenylbutyrate, sodium phosphate, sodium polystyrene sulfonate, sodium tetradecyl sulfate, sodium thiosulfate, sodium zirconium cyclosilicate, sofosbuvir, solifenacin succinate, somatropin, somatropin recombinant, sonidegib phosphate, sorafenib tosylate, sorbitol, sotalol hydrochloride, spinosad, spironolactone, stavudine, streptomycin sulfate, streptozocin, strontium chloride Sr-89, succimer, succinylcholine chloride, sucralfate, sucroferric oxyhydroxide, sufentanil citrate, sugammadex sodium, sulbactam, sulconazole nitrate, sulfacetamide sodium, sulfadiazine, sulfamethoxazole, sulfanilamide, sulfasalazine, sulfur hexafluoride lipid-type A microspheres, sulindac, sumatriptan, sumatriptan succinate, sunitinib malate, suvorexant, tacrolimus, tadalafil, tafluprost, taliglucerase alfa, tamoxifen citrate, tamsulosin hydrochloride, tapentadol hydrochloride, tasimelteon, tavaborole, tazarotene, technetium Tc-99m albumin, technetium Tc-99m bicisate, technetium Tc-99m disofenin, technetium Tc-99m exametazime, technetium Tc-99m mebrofenin, technetium Tc-99m medronate, technetium Tc-99m mertiatide, technetium Tc-99m oxidronate, technetium Tc-99m pentetate, technetium Tc-99m pyrophosphate, technetium Tc-99m sestamibi kit, technetium Tc-99m sodium pertechnetate, technetium Tc-99m sulfur colloid, technetium Tc-99m tetrofosmin, technetium Tc-99m tilmanocept, tedizolid phosphate, teduglutide recombinant, telavancin hydrochloride, telmisartan, telotristat etiprate, temazepam, temozolomide, temsirolimus, tenofovir alafenamide fumarate, tenofovir disoproxil fumarate, terazosin hydrochloride, terbinafine, terbinafine hydrochloride, terbutaline sulfate, terconazole, teriflunomide, teriparatide recombinant human, tesamorelin acetate, testosterone, testosterone cypionate, testosterone enanthate, testosterone undecanoate, tetrabenazine, tetracaine hydrochloride, tetracycline hydrochloride, tetrahydrozoline hydrochloride, thalidomide, thallous chloride Tl-201, theophylline, thiamine hydrochloride, thioguanine, thioridazine hydrochloride, thiotepa, thiothixene, thyrotropin alfa, tiagabine hydrochloride, ticagrelor, ticlopidine hydrochloride, tigecycline, timolol, timolol maleate, tinidazole, tioconazole, tiopronin, tiotropium bromide, tipiracil hydrochloride, tipranavir, tirofiban hydrochloride, tizanidine hydrochloride, tobramycin, tobramycin sulfate, tofacitinib citrate, tolazamide, tolbutamide, tolcapone, tolmetin sodium, tolterodine tartrate, tolvaptan, topiramate, topotecan hydrochloride, toremifene citrate, torsemide, trabectedin, tramadol hydrochloride, trametinib dimethyl sulfoxide, trandolapril, tranexamic acid, tranylcypromine sulfate, travoprost, trazodone hydrochloride, treprostinil, treprostinil diolamine, tretinoin, triamcinolone acetonide, triamcinolone hexacetonide, triamterene, triazolam, trientine hydrochloride, trifluoperazine hydrochloride, trifluridine, trihexyphenidyl hydrochloride, trimethadione, trimethobenzamide hydrochloride, trimethoprim, trimethoprim hydrochloride, trimipramine maleate, triptorelin pamoate, tromethamine, tropicamide, trospium chloride, trypan blue, ulipristal acetate, ultramicrosize, umeclidinium bromide, urea, uridine triacetate, ursodiol, valacyclovir hydrochloride, valbenazine tosylate, valganciclovir hydrochloride, valproate sodium, valproic acid, valrubicin, valsartan, hydrochlorothiazide, vancomycin hydrochloride, vandetanib, vardenafil hydrochloride, varenicline tartrate, vasopressin, vecuronium bromide, velaglucerase alfa, vemurafenib, venetoclax, venlafaxine hydrochloride, verapamil hydrochloride, verteporfin, vigabatrin, vilazodone hydrochloride, vinblastine sulfate, vincristine sulfate, vinorelbine tartrate, vismodegib, vitamin A palmitate, vorapaxar sulfate, voriconazole, vorinostat, vortioxetine hydrobromide, warfarin sodium, xenon Xe-133, zafirlukast, zaleplon, zanamivir, ziconotide acetate, zidovudine, zileuton, zinc acetate, zinc chloride, ziprasidone hydrochloride, ziprasidone mesylate, zoledronic acid, zolmitriptan, zolpidem tartrate, zonisamide, or a combination thereof.

The effects of chemotherapy on the human body can be quite dramatic and tragic, as is known to persons in the cancer treatment professions. The side effects can be painful and can cause a great amount of stress not only for the patient, but for the patient's family, friends and associates. This novel treatment has no aggressive properties and is not harmful to the patient. A subject composition may be administered to a chemotherapy patient to reduce the adverse events or side effects associated with chemotherapy treatment. A subject composition may be used in conjunction with any chemotherapy medication or drug, including actinomycin, abraxane, all-trans retinoic acid, alitretinoin, azacitidine, azathioprine, bexarotene, bleomycin, bortezomib, carboplatin, capecitabine, cisplatin, chlorambucil, cyclophosphamide, cytarabine, dacarbazine, daunorubicin, docetaxel, doxifluridine, doxorubicin, epirubicin, epothilone, erlotinib, etoposide, fluorouracil, gefitinib, gemcitabine, hydroxyurea, idarubicin, imatinib, irinotecan, mechlorethamine, melphalan, mercaptopurine, methotrexate, mitoxantrone, a nitrosourea, oxaliplatin, paclitaxel, pemetrexed, romidepsin, tafluposide, taxotere, temozolomide, teniposide, tioguanine, topotecan, tretinoin, valrubicin, vemurafenib, vinblastine, vincristine, vindesine, vinorelbine, vismodegib, vorinostat, or a combination thereof. In some embodiments, a subject composition is used in conjunction with R-Epoch or Epoch-R (rituximab and etoposide phosphate), Rituxan (rituximab and hyaluronidase human), a steroid, prednisone, etoposide, vincristine, vincristine sulfate, cyclophosphamide, doxorubicin, rituximab, CHOP regimen (cyclophosphamide, doxorubicin hydrochloride (hydroxydaunorubicin), vincristine sulfate (Oncovid), and prednisone), hydroxydaunorubicin, taxol, carboplatin, pemetrexed, paclitaxel (protein bound), taxotere, docetaxel, ramucirumab, or a combination thereof.

Example 1

A 52 year-old woman begins chemotherapy with actinomycin for treatment of ovarian cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant bone marrow suppression, vomiting, mouth ulcers, hair loss, liver problems, infections, and/or muscle pains.

Example 2

A 75 year-old man begins chemotherapy with all-trans retinoic acid for treatment of acute promyelocytic leukemia. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant shortness of breath, headache, numbness, depression, skin dryness, itchiness, hair loss, vomiting, muscle pains, and/or vision changes.

Example 3

A 61 year-old woman begins chemotherapy with azacitidine for treatment of myelodysplastic syndrome. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant anemia, neutropenia, thrombocytopenia, hetpatotoxicity, kidney toxicity, nausea, vomiting, fevers, diarrhea, redness at its injection sites, constipation, bruising, petechiae, rigors, weakness, and/or abnormally low potassium levels in the bloodstream.

Example 4

A 59 year-old man begins chemotherapy with bleomycin for treatment of Hodgkin's lymphoma. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant fever, weight loss, vomiting, rash, anaphylaxis, and/or inflammation.

Example 5

A 55 year-old woman begins chemotherapy with bortezomib for treatment of mantle cell lymphoma. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant nausea, diarrhea, tiredness, low platelets, fever, numbness, low white blood cells, shortness of breath, rash, abdominal pain, low blood pressure, tumor lysis syndrome, heart failure, and/or reversible posterior leukoencephalopathy syndrome.

Example 6

A 63 year-old man begins chemotherapy with carboplatin for treatment of brain cancer. He is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. He experiences no significant low blood cell levels, nausea, electrolyte problems, and/or allergic reactions.

Example 7

A 49 year-old woman begins chemotherapy with capecitabine for treatment of breast cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant abdominal pain, vomiting, diarrhea, weakness, rashes, blood clotting problems, allergic reactions, heart problems such as cardiomyopathy, and/or low blood cell counts.

Example 8

A 58 year-old man begins chemotherapy with cisplatin for treatment of testicular cancer. He is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. He experiences no significant bone marrow suppression, hearing problems, kidney problems, vomiting, numbness, trouble walking, allergic reactions, electrolyte problems, and/or heart disease.

Example 9

A 71 year-old woman begins chemotherapy with chlorambucil for treatment of chronic lymphocytic leukemia. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant bone marrow suppression and/or allergic reactions.

Example 10

A 68 year-old man begins chemotherapy with cyclophosphamide for treatment of multiple myeloma. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant low white blood cell counts, loss of appetite, vomiting, hair loss, bleeding from the bladder, allergic reactions, and/or pulmonary fibrosis.

Example 11

A 54 year-old woman begins chemotherapy with cytarabine for treatment of acute myeloid leukemia. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant bone marrow suppression, vomiting, diarrhea, liver problems, rash, ulcer formation in the mouth, bleeding, loss of consciousness, lung disease, and/or allergic reactions.

Example 12

A 70 year-old man begins chemotherapy with daunorubicin for treatment of Kaposi's sarcoma. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant hair loss, vomiting, bone marrow suppression, inflammation of the inside of the mouth, heart disease and/or tissue death at the site of injection.

Example 13

A 72 year-old woman begins chemotherapy with docetaxel for treatment of non-small-cell lung cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant hair loss, low blood cell counts, numbness, shortness of breath, vomiting, and/or muscle pains.

Example 14

A 77 year-old man begins chemotherapy with doxifluridine for treatment of pancreatic cancer. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant diarrhea, neurotoxicity and/or mucositis.

Example 15

A 69 year-old woman begins chemotherapy with doxorubicin for treatment of bladder cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant hair loss, bone marrow suppression, vomiting, rash, and inflammation of the mouth, anaphylaxis, heart damage, and/or tissue damage at the site of injection.

Example 16

A 60 year-old woman begins chemotherapy with for treatment with epirubicin for treatment of node-positive breast cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant hair loss, bone marrow suppression, vomiting, rash, and/or inflammation of the mouth.

Example 17

A 56 year-old woman begins chemotherapy with epothilone for treatment of metastatic breast cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant fatigue, nausea, cramping abdominal pain, constipation, myalgia, chills, and/or arthralgia.

Example 18

A 51 year-old man begins chemotherapy with etoposide for treatment of testicular promyelocytic leukemia. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant low blood cell counts, vomiting, loss of appetite, diarrhea, hair loss, fever, allergic reactions and/or low blood pressure.

Example 19

A 54 year-old woman begins chemotherapy with fluorouracil for treatment of stomach cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant inflammation of the mouth, loss of appetite, low blood cell counts, hair loss, inflammation of the skin, and/or irritation at the site of injection.

Example 20

A 56 year-old man begins chemotherapy with gemcitabine for treatment of bladder cancer. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant bone marrow suppression, liver and kidney problems, nausea, fever, rash, shortness of breath, mouth sores, diarrhea, neuropathy, and/or hair loss.

Example 21

A 59 year-old woman begins chemotherapy with hydroxyurea for treatment of cervical cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant bone marrow suppression, fevers, loss of appetite, psychiatric problems, shortness of breath, and/or headaches.

Example 22

A 52 year-old man begins chemotherapy with idarubicin for treatment of acute lymphoblastic leukemia. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant diarrhea, stomach cramps, nausea and/or vomiting.

Example 23

A 62 year-old woman begins chemotherapy with imatinib for treatment of chronic eosinophilic leukemia. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant vomiting, diarrhea, muscle pain, headache, rash, fluid retention, gastrointestinal bleeding, bone marrow suppression, liver problems, and/or heart failure.

Example 24

A 64 year-old man begins chemotherapy with irinotecan for treatment of colon cancer. He is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. He experiences no significant diarrhea, vomiting, bone marrow suppression, hair loss, shortness of breath, fever, blood clots, colon inflammation, and/or allergic reactions.

Example 25

A 61 year-old man begins chemotherapy with mechlorethamine for treatment of prostate cancer. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant rhinorrhea, epistaxis, toneless voice, dyspnea, inflammation, epithelial necrosis, erythema and/or vesication.

Example 26

A 55 year-old man begins chemotherapy with mercaptopurine for treatment of acute lymphocytic leukemia. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant bone marrow suppression, liver toxicity, vomiting, and/or loss of appetite.

Example 27

A 75 year-old woman begins chemotherapy with methotrexate for treatment of osteosarcoma. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant nausea, tiredness, fever, increased risk of infection, low white blood cell counts, breakdown of the skin inside the mouth, liver disease, lung disease, and/or severe skin rashes.

Example 28

A 64 year-old man begins chemotherapy with mitoxantrone for treatment of metastatic hormone-refractory prostate cancer. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant nausea, vomiting, hair loss, heart damage, immunosuppression, and/or cardiomyopathy.

Example 29

A 67 year-old woman begins chemotherapy with oxaliplatin for treatment of colorectal cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant numbness, tiredness, nausea, diarrhea, low blood cell counts, and/or allergic reactions.

Example 30

A 55 year-old man begins chemotherapy with paclitaxel for treatment of lung cancer. He is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. He experiences no significant nausea, vomiting, loss of appetite, change in taste, thinned or brittle hair, pain in the joints of the arms or legs, changes in the color of the nails, tingling in the hands or toes, unusual bruising or bleeding, pain, redness or swelling at the injection site, hand-foot syndrome, change in normal bowel habits, fever, chills, cough, sore throat, difficulty swallowing, dizziness, shortness of breath, severe exhaustion, skin rash, facial flushing, chest pain, and/or neuropathy.

Example 31

A 66 year-old woman begins chemotherapy with pemetrexed for treatment of pleural mesothelioma. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant low blood cell counts, mental fatigue, sleepiness, nausea, vomiting, diarrhea, oral mucositis, loss of appetite, skin rash, and/or constipation.

Example 32

A 49 year-old man begins chemotherapy with teniposide for treatment of a brain tumor. He is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. He experiences no significant bone marrow suppression, gastrointestinal toxicity, hypersensitivity reactions, and/or alopecia.

Example 33

A 51 year-old woman begins chemotherapy with tioguanine for treatment of chronic myeloid leukemia cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant bone marrow suppression, liver problems, and/or inflammation of the mouth.

Example 34

A 50 year-old woman begins chemotherapy with topotecan for treatment of ovarian cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant neutropenia, leukopenia, anemia, thrombocytopenia, diarrhea, nausea, vomiting, stomatitis, constipation, increased susceptibility to infections, and/or asthenia.

Example 35

A 70 year-old woman begins chemotherapy with valrubicin for treatment of bladder cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant blood in her urine, incontinence, painful or difficult urination, and/or unusually frequent urination.

Example 36

A 42 year-old man begins chemotherapy with vemurafenib for treatment of melanoma. He is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. He experiences no significant skin lesions, arthralgia, skin rash, photosensitivity, and/or signs of liver toxicity.

Example 37

A 59 year-old man begins chemotherapy with vinblastine for treatment of testicular cancer. He is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. He experiences no significant change in sensation, constipation, weakness, loss of appetite, headaches, low blood cell counts and/or shortness of breath.

Example 38

A 68 year-old woman begins chemotherapy with vincristine for treatment of small cell lung cancer. She is administered about 0.5-3 ounces of an aqueous solution containing sodium bicarbonate, sodium carbonate, and trisodium phosphate in a 1:1:1 weight ratio, so that the total concentration of the three components was 64 grams/gallon, 3-6 times a day, such as before and/or after every meal for the duration of the chemotherapy. She experiences no significant change in sensation, hair loss, constipation, difficulty walking, headaches, neuropathic pain, lung damage, and/or low white blood cells.

Example 39

A 48 year-old woman begins chemotherapy with vindesine for treatment of leukemia. She is administered about 0.5-3 ounces of an aqueous solution containing sodium bicarbonate, sodium carbonate, and tri sodium phosphate in a 1:1:1 weight ratio, so that the total concentration of the three components was 64 grams/gallon, 3-6 times a day, such as before and/or after every meal for the duration of the chemotherapy. She experiences no significant bruising, bleeding, breathlessness, numbness, diarrhea, constipation, mouth sores and ulcers, loss of appetite, indigestion, difficulty swallowing, pain, hair loss, skin rash, inflammation around the injection site, depression, headaches, weakness, seizures, hearing changes, and/or dizziness.

The following embodiments are specifically contemplated:

Embodiment 1

A method for reducing an adverse event associated with use of a medication, comprising: administering to a patient taking the medication, a buffered aqueous liquid having a pH of about 10 to 11.5, wherein the buffered aqueous liquid comprises sodium bicarbonate, sodium carbonate, and trisodium phosphate.

Embodiment 2

The method of Embodiment 1, wherein the buffered aqueous liquid further comprises hydrogen bond activated water.

Embodiment 3

The method of Embodiment 1, wherein the buffered aqueous liquid is orally administered to the patient one to three times per waking day.

Embodiment 4

The method of Embodiment 1, wherein the medication comprises carboplatin.

Embodiment 5

The method of Embodiment 1, wherein the medication comprises cisplatin.

Embodiment 6

The method of Embodiment 1, wherein the medication comprises cyclophosphamide.

Embodiment 7

The method of Embodiment 1, wherein the medication comprises docetaxel.

Embodiment 8

The method of Embodiment 1, wherein the medication comprises doxorubicin.

Embodiment 9

The method of Embodiment 1, wherein the medication comprises etoposide.

Embodiment 10

The method of Embodiment 1, wherein the medication comprises fluorouracil.

Embodiment 11

The method of Embodiment 1, wherein the medication comprises gemcitabine.

Embodiment 12

The method of Embodiment 1, wherein the medication comprises methotrexate.

Embodiment 13

The method of Embodiment 1, wherein the medication comprises paclitaxel.

Embodiment 14

The method of Embodiment 1, wherein the medication comprises capecitabine.

Embodiment 15

The method of Embodiment 1, wherein the medication comprises vinorelbine.

Embodiment 16

The method of Embodiment 1, wherein the medication comprises epirubicin.

Embodiment 17

The method of Embodiment 1, wherein the medication comprises bleomycin.

Embodiment 18

The method of Embodiment 1, wherein the medication comprises vinblastine.

Embodiment 19

The method of Embodiment 1, wherein the medication comprises dacarbazine.

Embodiment 20

The method of Embodiment 1, wherein the medication comprises vincristine.

While the above description contains many specifics, these should not be construed as limitations on the scope of the disclosure, but rather as an exemplification of the embodiments therein. It is to be understood that the invention is not limited to these specific embodiments. Accordingly, the invention is not limited to the precise embodiments described in detail hereinabove. With respect to the claims, it is applicant's intention that the claims not be interpreted in accordance with the sixth paragraph of 35 U.S.C. § 112 unless the term "means" is used followed by a functional statement. Further, with respect to the claims, it should be understood that any of the claims described below may be combined for the purposes of the invention.

The invention claimed is:

1. A method for reducing an adverse event associated with use of a medication, comprising: administering to a patient taking the medication, a buffered aqueous liquid having a pH of about 10 to 11.5, wherein the buffered aqueous liquid comprises sodium bicarbonate, sodium carbonate, and trisodium phosphate, wherein the total amount of sodium bicarbonate, sodium carbonate, and trisodium phosphate in the buffered aqueous liquid is about 0.05 grams/ounce to about 0.8 grams/ounce.

2. The method of claim 1, wherein the buffered aqueous liquid further comprises hydrogen bond activated water.

3. The method of claim 1, wherein the buffered aqueous liquid is orally administered to the patient one to three times per waking day.

4. The method of claim 1, wherein the medication comprises carboplatin.

5. The method of claim 1, wherein the medication comprises cisplatin.

6. The method of claim 1, wherein the medication comprises cyclophosphamide.

7. The method of claim 1, wherein the medication comprises docetaxel.

8. The method of claim 1, wherein the medication comprises doxorubicin.

9. The method of claim 1, wherein the medication comprises etoposide.

10. The method of claim 1, wherein the medication comprises fluorouracil.

11. The method of claim 1, wherein the medication comprises gemcitabine.

12. The method of claim 1, wherein the medication comprises methotrexate.

13. The method of claim 1, wherein the medication comprises paclitaxel.

14. The method of claim 1, wherein the medication comprises capecitabine.

15. The method of claim 1, wherein the medication comprises vinorelbine.

16. The method of claim 1, wherein the medication comprises epirubicin.

17. The method of claim 1, wherein the medication comprises bleomycin.

18. The method of claim 1, wherein the medication comprises vinblastine.

19. The method of claim 1, wherein the medication comprises dacarbazine.

20. The method of claim 1, wherein the medication comprises vincristine.

21. The method of claim 1, wherein the medication comprises actinomycin, abraxane, all-trans retinoic acid, alitretinoin, azacitidine, azathioprine, bexarotene, bortezomib, chlorambucil, cytarabine, dacarbazine, daunorubicin, doxifluridine, epothilone, erlotinib, gefitinib, hydroxyurea, idarubicin, imatinib, irinotecan, mechlorethamine, melphalan, mercaptopurine, mitoxantrone, a nitrosourea, oxaliplatin, pemetrexed, romidepsin, tafluposide, taxotere, temozolomide, teniposide, tioguanine, topotecan, tretinoin, valrubicin, vemurafenib, vincristine, vindesine, vismodegib, vorinostat, or a combination thereof.

* * * * *